United States Patent [19]

Sullivan et al.

[11] Patent Number: 4,643,569

[45] Date of Patent: Feb. 17, 1987

[54] DUAL BEAM LASER INSPECTION APPARATUS

[75] Inventors: Sean Sullivan, Glendale; Glenn E. Stutz, Scottsdale, both of Ariz.

[73] Assignee: Lincoln Laser Company, Phoenix, Ariz.

[21] Appl. No.: 746,177

[22] Filed: Jun. 18, 1985

[51] Int. Cl.⁴ ........................................... G01N 21/88
[52] U.S. Cl. .................................... 356/237; 250/563; 350/6.8
[58] Field of Search ................ 356/237; 250/563, 572; 350/6-8

[56] References Cited

U.S. PATENT DOCUMENTS

| | | | |
|---|---|---|---|
| 3,573,849 | 4/1969 | Herriot | 346/108 |
| 3,597,536 | 8/1971 | Fowler | 178/7.3 D |
| 3,646,568 | 2/1972 | Woywood | 346/108 |
| 3,750,189 | 7/1973 | Fleischer | 346/74 |
| 3,781,464 | 12/1973 | Bousky | 178/5.4 |
| 3,865,465 | 2/1975 | Tatuoka et al. | 350/7 |
| 4,013,367 | 3/1977 | Nagao et al. | 356/200 |
| 4,040,096 | 8/1977 | Starkweather | 358/302 |
| 4,054,360 | 10/1977 | Oosaka et al. | 350/7 |
| 4,054,361 | 10/1977 | Noguchi | 350/7 |
| 4,063,226 | 12/1977 | Kozma et al. | 365/125 |
| 4,101,193 | 7/1978 | Waterworth et al. | 350/6.8 |
| 4,121,883 | 10/1978 | Goshima et al. | 350/6.8 |
| 4,123,135 | 10/1978 | Rabedeau | 350/6.8 |
| 4,260,899 | 4/1981 | Baker | 250/563 |
| 4,277,128 | 7/1981 | Kawamura | 350/6.8 |
| 4,277,178 | 7/1981 | Cushing et al. | 356/431 |
| 4,281,889 | 8/1981 | Noguchi | 350/6.8 |
| 4,284,994 | 8/1981 | Radl | 346/108 |
| 4,294,506 | 10/1981 | Hattori | 350/6.8 |
| 4,538,909 | 9/1985 | Bible et al. | 356/237 |
| 4,556,903 | 12/1985 | Blitchington et al. | 356/237 X |

*Primary Examiner*—Davis L. Willis
*Assistant Examiner*—Matthew W. Koren

*Attorney, Agent, or Firm*—Cahill, Sutton & Thomas

[57] ABSTRACT

An optical input beam is split into first and second beams lying in first and second non-parallel planes. A polygon mirror scanner receives the first and second beams on a single facet and generates first and second angularly displaced, non-parallel synchronized scans. Redirecting means is positioned in the optical path between the scanner and a scanned plane for redirecting a portion of the first and second synchronized scans onto a timing plane to generate third and fourth non-coincident, synchronized scans. A beam position signal consisting of equally spaced, sequential pulses is generated in response to the travel of either the third or fourth synchronized scan along a second scanned line lying within a timing plane. The beam position signal is representative of the position of both the first and second synchronized scans along the first scanned line. The second section of the laser inspection apparatus reads information from a surface having an area illuminated by the dual beams of the optical scanner. The first and second synchronized scans from the optical scanner cause the illuminated area to emit radiation in the form of first and second modulated scans. Segmented radiation detection means includes first, second and sandwiched radiation detection means which each generated an electrical output signal representative of the detected radiation emitted by the first and second modulated scans. Signal processing means receives and selectively combines the electrical output signals from each of the three sections of the segmented radiation detection means in response to the beam position signal and generates first and second modulated output signals. The first modulated output signal is representative of the information residing within the area scanned by the first scan, while the second modulated signal is representative of the information residing within the area scanned by the second scan.

35 Claims, 28 Drawing Figures

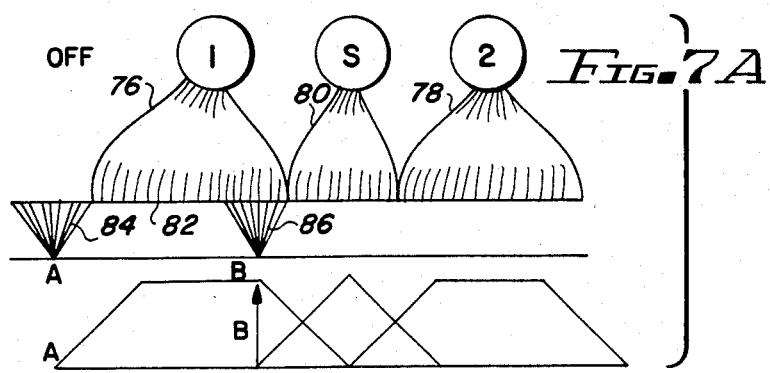
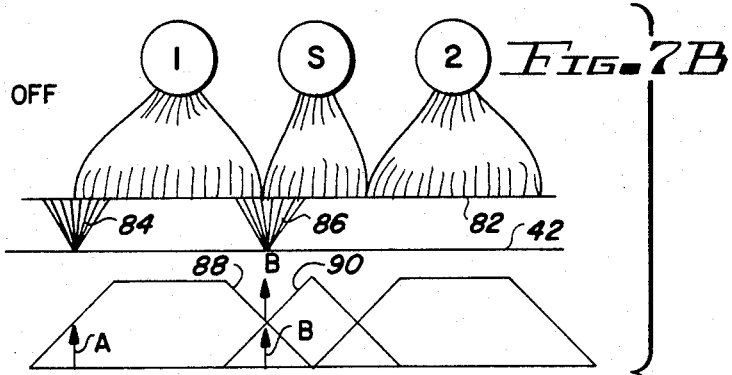
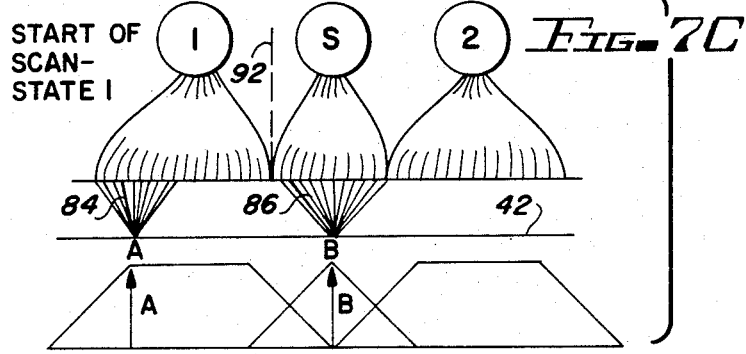
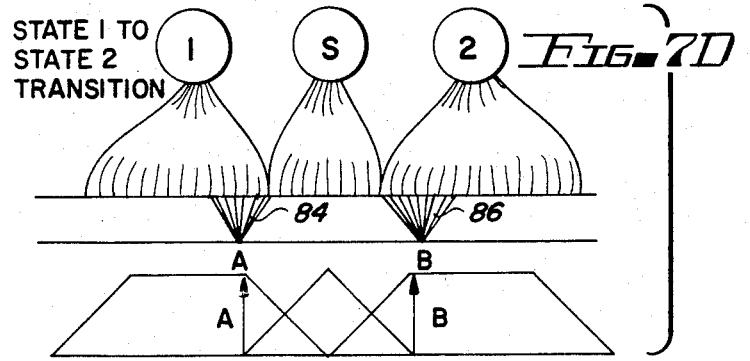
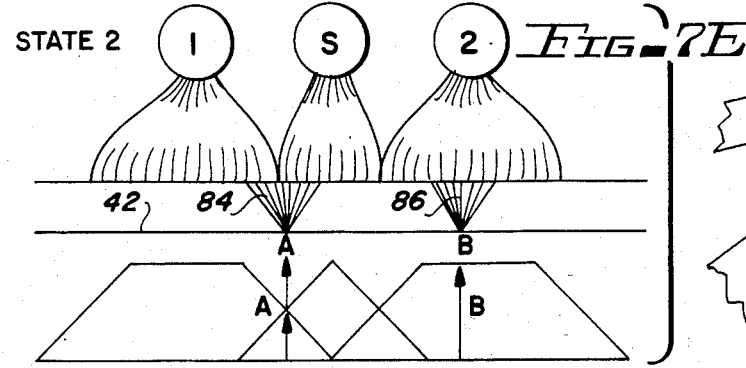
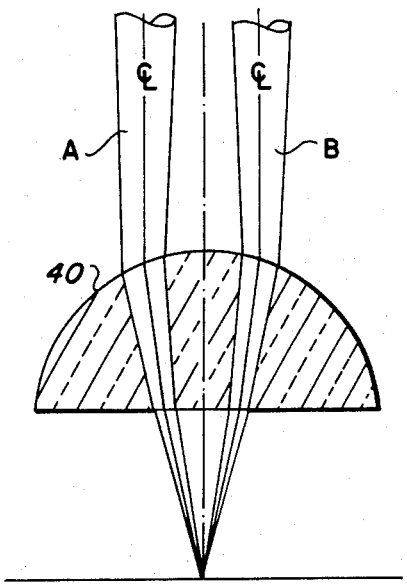
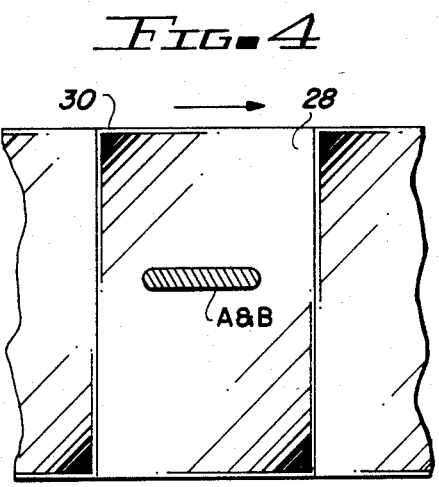
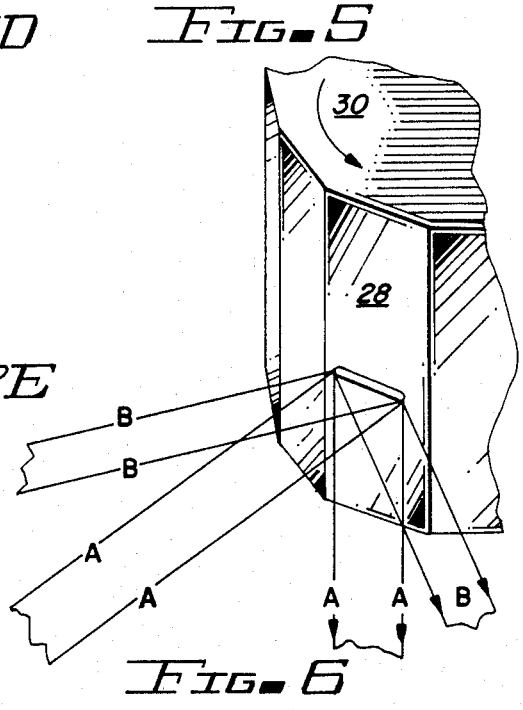

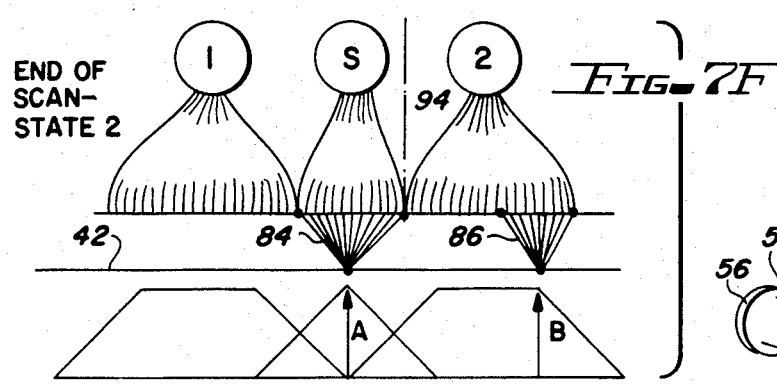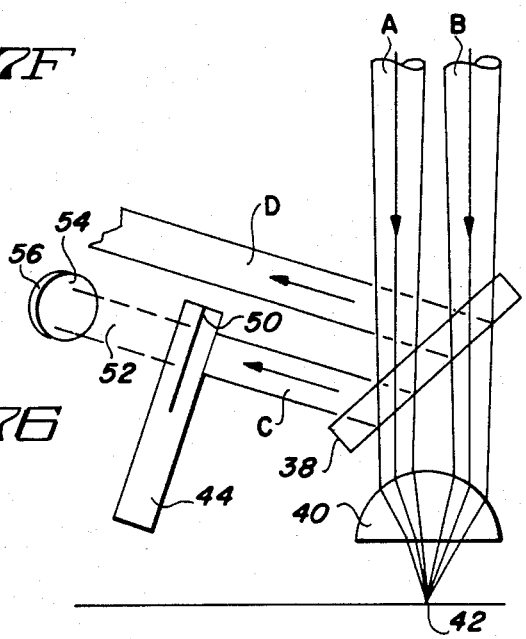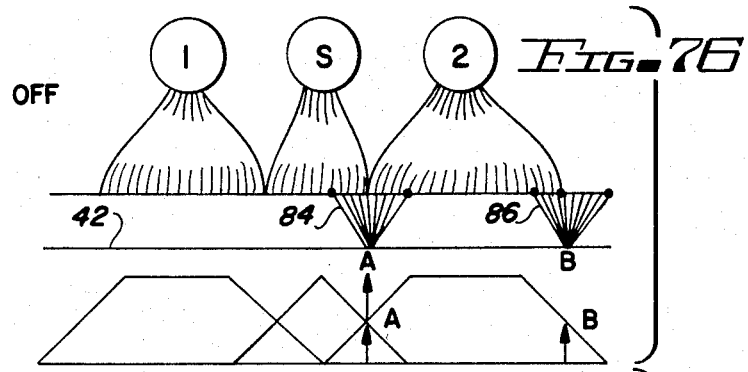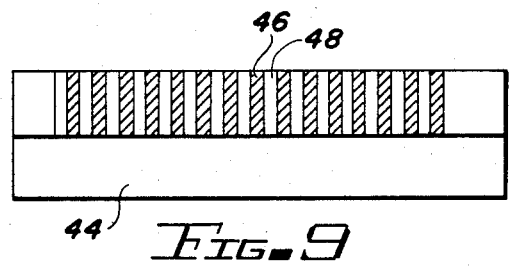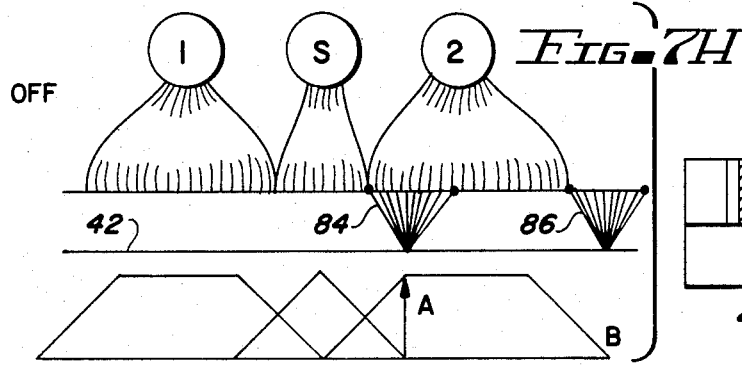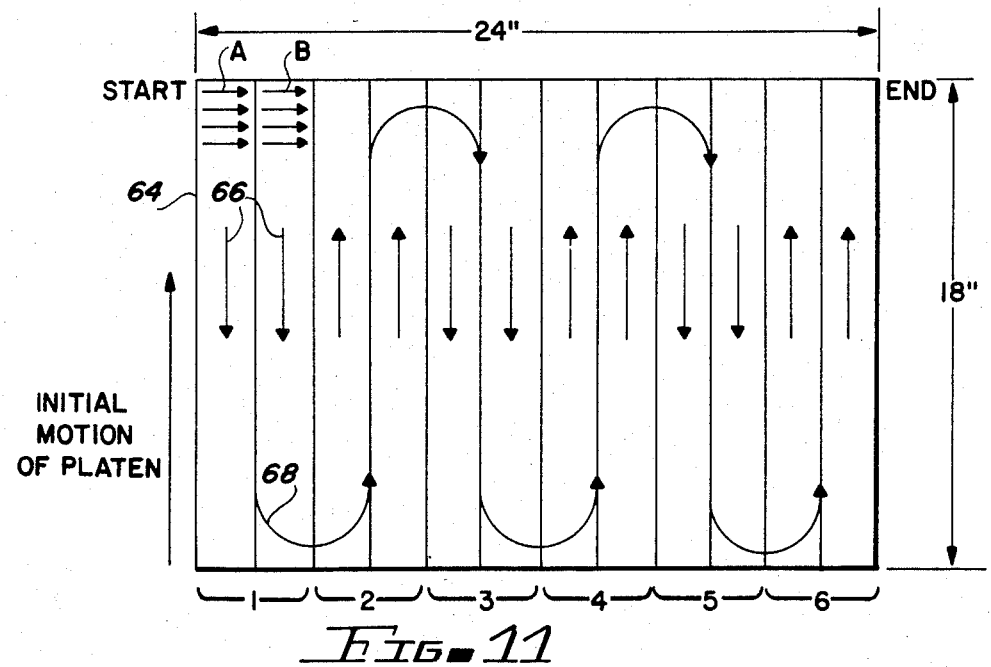

DUAL BEAM LASER INSPECTION APPARATUS

BACKGROUND OF THE INVENTION

1. Field of the Invention

This invention relates to laser scanning and inspection apparatus, and more particularly, to dual beam laser inspection apparatus for reading information from a two dimensional surface.

2. Description of the Prior Art

A key design objective of laser inspection equipment is to complete the inspection of a defined area in a minimum amount of time. To accomplish this goal, prior art laser inspection equipment incorporates a single beam scanner. Increased inspection rates are achieved by increasing the scan velocity. An increased scan velocity produces faster data input rates and requires a corresponding increase in data processing rate. Such high speed processing operations frequently present design difficulties and significantly increase the overall cost of the inspection apparatus.

SUMMARY OF THE INVENTION

It is therefore a major object of the present invention to provide a dual beam laser inspection apparatus including a scanner which repetitively scans a line with first and second angularly displaced, synchronized scans.

Another object of the present invention is to provide a dual beam laser inspection apparatus which processes data received from each of the dual scanning beams in parallel to thereby reduce the data processing rate by fifty percent in comparison to a single beam laser inspection apparatus operating at the same inspection rate.

Still another object of the present invention is to avoid problems of clock competition which normally occur in dual beam laser inspection apparatus if a periodic structure such as a ruled grating is used. This invention ensures that only one beam is available to generate a beam position signal to coordinate the data processing section of the inspection apparatus with the position of each of the dual scanning beams along the inspected surface.

Yet another object of the present invention is to provide a dual beam laser inspection apparatus which directs a portion of one of the scanning beams across a ruled transmission grating and into a photomultiplier tube to convert the scanned optical beam into a pulsed electrical timing signal representative of the position of each of the dual beams.

Yet another object of the present invention is to provide a dual beam laser inspection apparatus which includes segmented radiation collection means having first and second radiation detection means and a sandwiched radiation detection means positioned between the first and second radiation detection means for generating electrical output signals representative of electromagnetic energy generated in response to displacements of the dual beams across the inspected surface.

Another object of the present invention is to provide a dual beam laser inspection apparatus wherein the electrical output signals from the first, second and sandwiched radiation detection means are selectively combined by signal processing means in response to a beam position signal to generate a first output signal representative of information on the area swept by the first scanned beam and to generate a second output signal representative of the information on the area swept by the second scanned beam.

Still another object of the present invention is to provide a dual beam laser inspection apparatus which generates a dual scanning beam by utilizing a single polygon mirror scanner which receives first and second optical input beams on a single facet and generates first and second angularly displaced, non-parallel synchronized scans.

Still another object of the present invention is to provide a dual beam inspection apparatus which includes segmented radiation collection means incorporating three adjacent photomultiplier tube assemblies wherein the intermediate or sandwiched photomultiplier tube assembly collects radiation alternately generated in response to the first and then the second of the dual beams within a beam overlap zone to thereby totally eliminate cross talk between the two outboard photomultiplier tube assemblies.

Briefly stated, and in accord with one embodiment of the invention, a dual beam laser inspection apparatus includes a light source for generating an input beam and means for receiving the input beam and generating first and second beams lying in first and second non-parallel planes. A polygon mirror scanner receives the first and second beams on a single facet and generates first and second angularly displaced, non-coincident synchronized scans. Redirecting means is positioned in the optical path between the scanner and the scanned plane and redirects a portion of the first and second synchronized scans onto a timing plane to generate third and fourth non-coincident synchronized scans. Beam position signal generating means produces equally spaced, sequential pulses in response to the travel of the third or fourth synchronized scans along a second scanned plane within the timing plane. The beam position signal is representative of the position of both the first and second synchronized scans along the scanned plane.

The laser inspection apparatus also includes apparatus for reading information from the scanned surface by processing radiation in the form of first and second modulated beams emitted in response to the scanned dual beams. The information reading section of the laser inspection apparatus includes segmented radiation collection means which receives the first and second modulated scans. Sandwiched radiation detection means includes first and second boundaries and is positioned to collect radiation alternately emitted by the first and second modulated scans within a beam overlap zone defined by the beginning of the second modulated scan and by the end of the first modulated scan. The sandwiched radiation detection means generates an electrical output signal representative of the first and second modulated scans within the beam overlap zone. The segmented radiation detection means further includes first and second radiation detection means. The first radiation detection means includes a third boundary positioned to collect radiation emitted by the first modulated scan from the beginning of the scan and a fourth boundary positioned adjacent to the first boundary of the sandwiched radiation detection means. The first radiation detection means generates an electrical output signal representative of the first modulated scan as it moves between the third and fourth boundaries. The second radiation detection means includes a fifth boundary positioned adjacent to the second boundary of the sandwiched radiation detection means and a sixth boundary positioned to collect radiation emitted by the second modulated scan at the end of the scan. The second radiation detection means generates an electrical output signal representative of the second modulated scan as it moves between the fifth and the sixth boundaries. Signal processing means receives the electrical output signals from the first and second radiation detection means and from the sandwiched radiation detection means and selectively combines these signals in response to the beam position signal to generate first and second modulated output signals. The first modulated output signal is representative of the information residing within the area scanned by the first scan while the second modulated signal is representative of the information residing within the area scanned by the second scan.

DESCRIPTION OF THE DRAWINGS

The invention is pointed out with particularity in the appended claims. However, other objects and advantages together with the operation of the invention may be better understood by reference to the following detailed description taken in connection with the following illustrations, wherein:

FIG. 4 is partially cutaway, enlarged view of the cylindrical lens depicted within the lower section of FIG. 2.

FIG. 5 is a partially cutaway, enlarged front sectional view of the polygon mirror scanner depicted in FIG. 1.

FIG. 6 is an enlarged, partially cutaway perspective view of the polygon mirror scanner depicted in FIG. 1, particularly illustrating the manner in which said scanner generates the first and second angularly displaced synchronized scans.

FIGS. 7A-7H represents a time-coordinated series of illustrations depicting the manner in which the segmented collecting means of the present invention receives and segregates information from the first and second modulated scans.

FIG. 8 is a compressed depiction of the scanned plane, the beam splitter and the ruled transmission grating depicted in FIG. 2, particularly illustrating how the third and fourth scanned beams are produced from the first and second scanned beams. This figure is not drawn to scale.

FIG. 9 is a front elevational view of the ruled transmission grating depicted in FIG. 8.

FIG. 11 is a view from above of a surface being inspected by the laser inspection apparatus of the present invention, particularly illustrating the relative alignment of the dual output beams of the inspection apparatus and the scanning pattern implemented by the inspection apparatus to cover the entire area of the surface being inspected.

DESCRIPTION OF THE PREFERRED EMBODIMENT

In order to better illustrate the advantages of the invention and its contributions to the art, a preferred hardware embodiment of the invention will now be described in detail.

Figure 1:
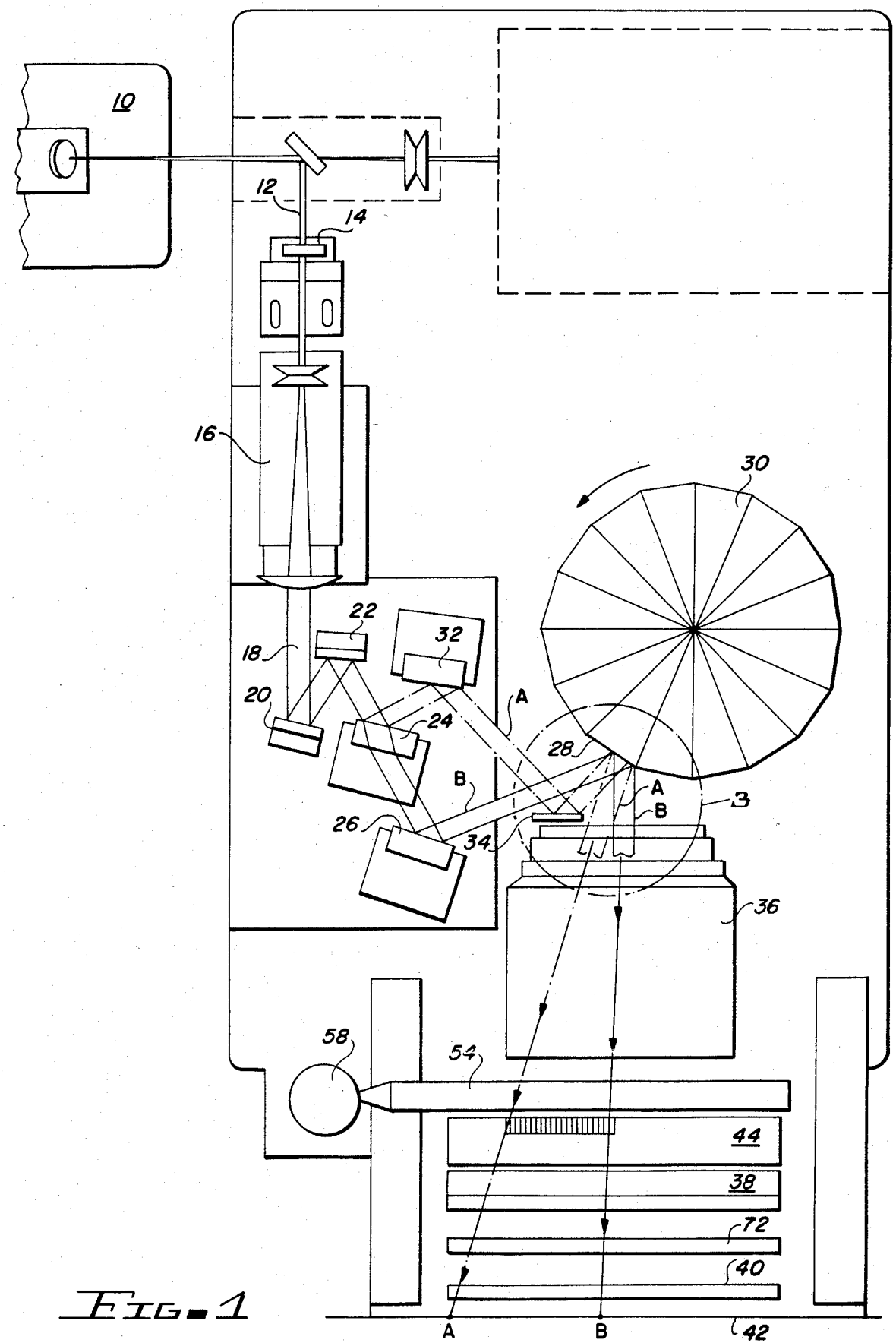
FIG. 1 is a front elevational view of the laser inspection apparatus of the present invention.
Figure 2:
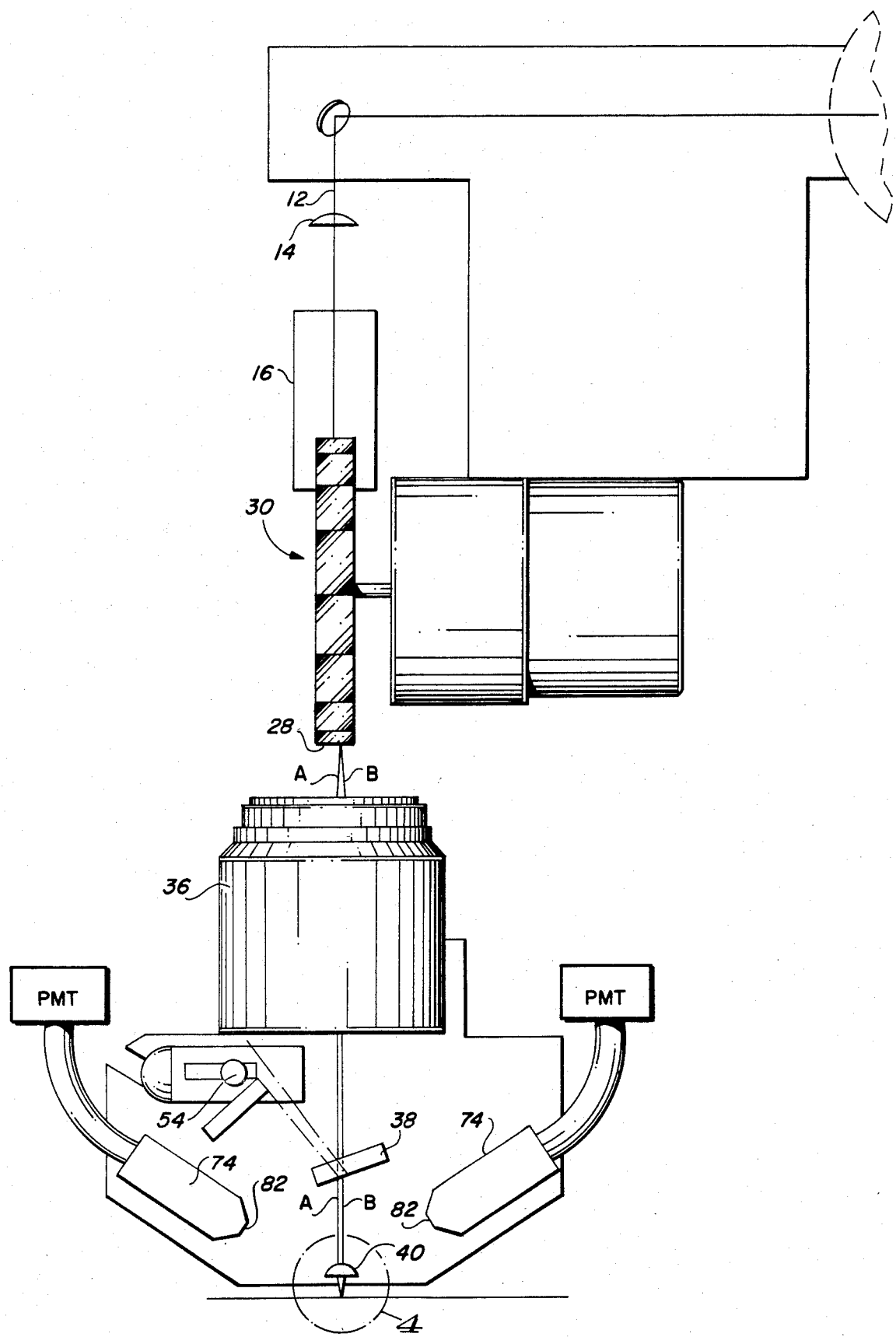
FIG. 2 is a side elevational view of the laser inspection apparatus depicted in FIG. 1.

Referring now to FIGS. 1 and 2, a light source in the form of a laser 10 generates an input beam 12 which is directed through a first cylindrical lens 14 and then through a telescopic beam expander 16.

As best illustrated in FIGS. 1 and 2, the expanded beam 18 is directed onto a relay mirror 20 and reflected by a second relay mirror 22 onto a beam splitter 24.

A first beam reflected by a beam splitter 24 is subsequently intercepted and reflected by relay mirrors 32 and 34 onto facet 28 as more specifically illustrated in FIG. 3. This first beam is subsequently referred to as beam "A". A second beam subsequently referred to as beam "B" passes through beam splitter 24 and is reflected by relay mirror 26 onto facet 28 of polygon mirror scanner 30.

Figure 16A:
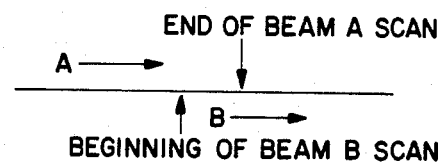
FIGS. 16A-C depict various types of scanning configurations which could be used in connection with the present invention.

The beam splitter 24 and series of mirrors 26, 32 and 34 are aligned (1) to provide the relative angular displacement between beams A and B as illustrated in FIGS. 1 and 6 and (2) to create a known artificially induced error analogous to facet to axis error by causing beams A and B to intercept facet 28 of polygon mirror 30 non-orthogonally with respect to the vertical plane. This error is purposely introduced to create a relative displacement between beams A and B at beam splitter 38 as is discussed in detail below. Relay mirrors 26, 32 and 34 are also aligned to cause beams A and B to coincide on facet 28 as depicted in FIG. 6. This coincident beam alignment on facet 28 produces scanned output beams A and B which are linearly aligned as depicted in FIG. 16A. This particular alignment is used in the preferred embodiment of the invention but is not required to implement the present invention.

Figure 3:
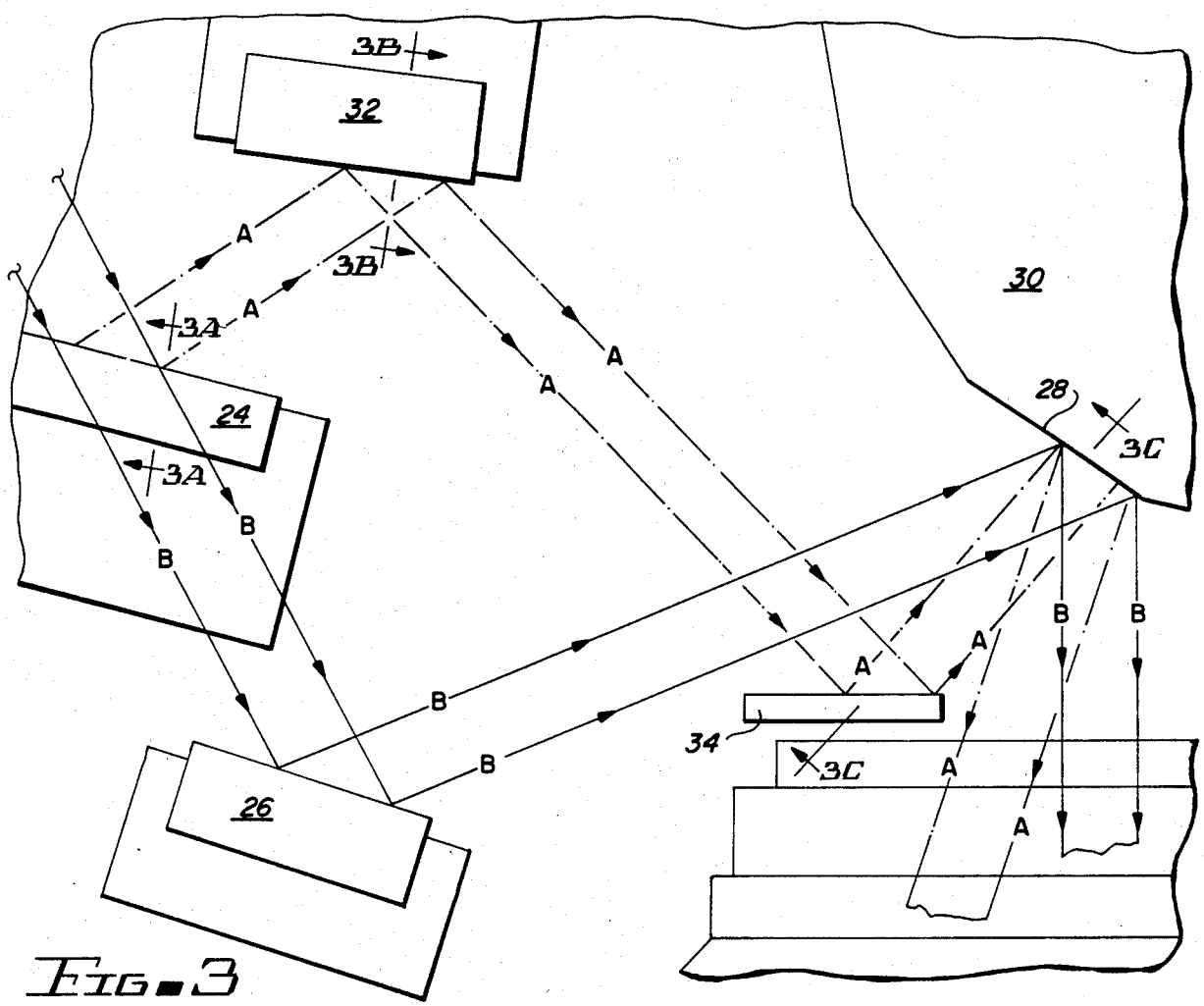
FIG. 3 is a partially cutaway, enlarged view of the beam splitter and series of mirrors illustrated in the central section of FIG. 1, particularly illustrating the manner in which the incoming light beam is divided into beams and directed onto a single facet of the polygon mirror scanner.

Referring now to FIGS. 1, 3 and 6, the constant angular velocity rotation of polygon mirror scanner 30 in combination with the incidence of angularly offset input beams A and B onto mirror facet 28 generate first and second angularly displaced, non-coincident synchronized scans designated as scans A and B.

Figure 14:
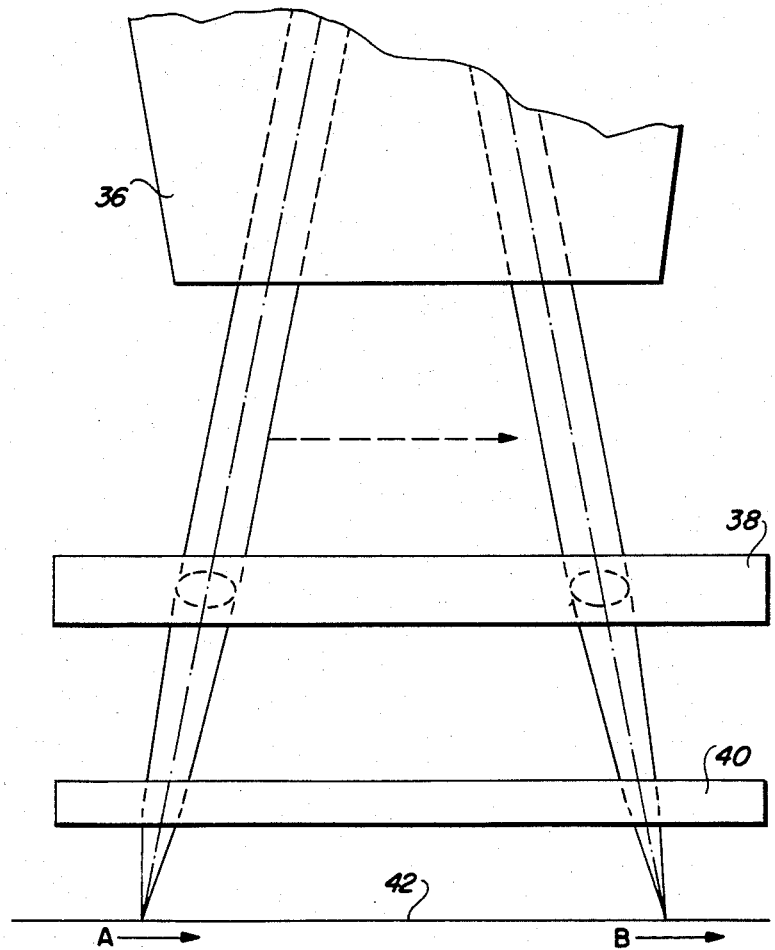
FIG. 14 is an enlarged, partially cutaway view of the laser inspection apparatus, particularly illustrating the radial or angular displacement between the first and second synchronized scans produced by the polygon mirror scanner.

As indicated by FIGS. 1, 2 and 14, angularly displaced, non-parallel synchronized scans A and B are directed through scan lens 36 and through redirecting means in the form of a beam splitter 38 which in the preferred embodiment of the invention constitutes a transparent glass plate which reflects approximately four percent of incident beams A and B to create redirected beams C and D. Beams A and B pass through beam splitter 38 and are reconverged by second cylindrical lens 40 onto scanned line 42 as most clearly illustrated in FIG. 8. Lens 40 forms the second half of facet to axis error correction means and totally eliminates the facet to axis equivalent error that was purposely introduced into the system by mirrors 26, 32 and 38 to provide an offset between scanned beams A and B at beam splitter 38 as described below.

First cylindrical lens 14 and second cylindrical lens 40 operate in combination as the first and second elements of facet to axis error correction means to essentially eliminate the facet to axis errors of each mirror facet 28 of polygon mirror scanner 30. In addition, this particular implementation of facet to axis error correction means serves an important reconverging function to reconverge beams A and B onto the scanned line 42 while still permitting the central rays of scanned beams A and B to be separated as they pass through beam splitter 38. The need for this physical separation between beams A and B at beam splitter 38 is explained immediately below.

Referring now to FIGS. 1, 2, 8 and 9, the beam position generating means of the present invention will now be described in detail. Although beams C and D have been redirected with respect to beams A and B, beams C and D maintain the same angularly displaced, non-coincident, synchronized relationship with beams A and B. As best illustrated in FIG. 8, beam C intercepts ruled transmission grating 44 while beam D is offset from beam C by a sufficient distance such that beam D does not intercept grating 44. It is important to realize that beam D is angularly offset from beam C at all times as is the case with beams A and B.

In the preferred embodiment of the invention, ruled transmission grating 44 includes alternate opaque or reflective strips 46 and transparent strips 48 each having a width of 0.001 inches. Strips 46 and 48 typically reside on the forward surface of grating 44 but have been symbolically represented by line 50 in FIG. 8. Beam C travels a total distance of 0.002 inches as it travels across one opaque strip 46 and an adjacent transparent strip 48 and generates a single optical pulse 52 which exits the rear surface of grating 44. As illustrated by FIG. 8, grating 44 is aligned to avoid intercepting any part of scanned beams A or B.

In the preferred embodiment of the invention, the length of the ruled section of transmission grating 44 equals 2.176 inches. Of this overall total distance, 0.12 inches corresponds to 64 digital bits and is required to stabilize the clock timing generator. The next 2.048 inch length of the ruled section of transmission grating 44 is used for system timing purposes and generates a 4096 bit beam position signal. At the start of scan position, beam D in the line scan direction is displaced 2.048 inches inboard on grating 44. Because the central rays of beams A and B are spaced apart at beam splitter 38, beam splitter 38 may be oriented to direct scanned beam D above grating 44 so that beam D avoids intercepting any of the ruled section of that grating, thereby avoiding any interference with the beam position signal generated by beam C.

Referring now to FIGS. 1 and 2, a transparent glass rod 54 is positioned immediately behind the ruled section of transmission grating 44 and receives the optical pulses generated as beam C scans across line 50 of grating 44. White paper or paint is applied to the rear surface 56 of rod 54 to diffusely reflect incoming optical pulses and thereby illuminate the entire interior of the rod. By internal reflection, some of this reflected light enters photomultiplier tube 58 which is coupled to the open cylindrical end of rod 54 as depicted in FIG. 1. The electrical output signal from photomultiplier tube 58 represents the beam position signal and consists of equally spaced, sequential timing pulses generated in response to the travel of scanned beam C along a scanned line on the ruled face of grating 44.

Because beam C represents merely a redirected element of scanned beam A and as a result of the synchronized relationship between scanned beams A and B, the beam position signal generated by photomultiplier tube 58 is representative of the position of scanned beams A and B along both the section of scanned line 42 scanned by beam A and along the section of scanned line 42 scanned by beam B.

It is important in practicing the present invention that relay mirrors 26, 32 and 36 or equivalent optical elements introduce a sufficient facet to axis related error to provide for an adequate clearance between redirected beams C and D so that beam D avoids intercepting the ruled section of grating 44. If this is not accomplished, competing optical pulses from both beams C and D will be directed to rod 54 causing photomultiplier tube 58 to generate a potentially unusable output signal.

The start of scan pulse which initiates the data acquisition timing is derived from the sixty-fourth pulse from grating 44.

FIG. 11 illustrates the sequence in which the laser scanning apparatus scans a two dimensional surface containing information. Typically, the laser inspection apparatus of the present invention is used to inspect a printed circuit board which incorporates a complex pattern of copper in combination with exposed, non-conductive fiberglass substrate. The output wavelength of laser 10 may be selected such that the underlying fiberglass substrate of printed circuit board 64 absorbs that wavelength and generates florescent radiation in response.

As illustrated in the upper lefthand corner of FIG. 11, radially displaced, synchronized scans A and B are linearly aligned and generate paired scans. In the preferred embodiment of the invention, scans A and B each have a length of 2.048 inches with an overlap of 0.048 inches. The total length of the scanned line formed by scanned beams A and B has therefore been configured to exactly equal 4.048 inches. At the end of each 4.048 inch scan of beams A and B, a platen to which circuit board 64 is secured advances the board as indicated by arrows 66 a predetermined distance and the inspection apparatus scans the next laterally displaced section of printed circuit board 64. After an entire 4.048 inch wide linear section of circuit board 64 has been scanned, the platen laterally advances board 64 as indicated by arrow 68 and another 4.048 inch wide section of the board of scanned. This pattern is repeated until the entire surface of printed circuit board 64 has been scanned.

The apparatus incorporated in the laser inspection apparatus of the present invention for reading information from the surface of printed circuit board 64 will now be described in detail.

Figure 12:
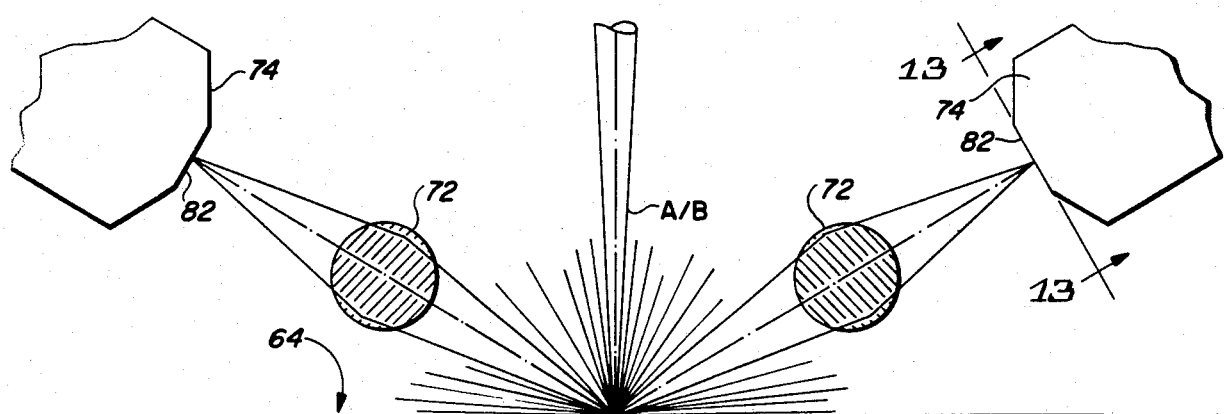
FIG. 12 is a partially cutaway, enlarged elevational view of the scanned plane, particularly illustrating the relative alignment between the dual output beams of the laser inspection apparatus and the segmented radiation collection means of the present invention.
Figure 13:
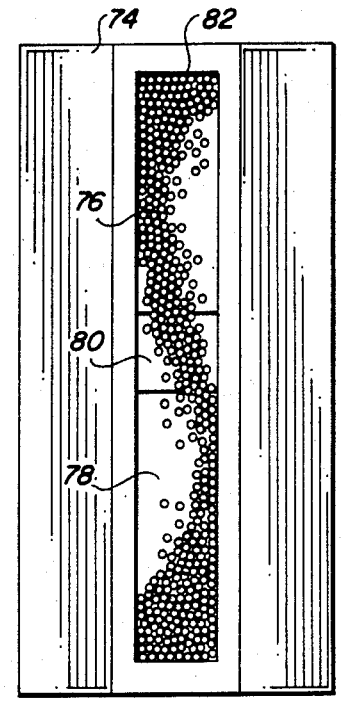
FIG. 13 is a view of the segmented radiation collection means depicted in FIG. 12, taken along section line 13—13.

FIG. 12 illustrates that the illumination of scanned line 42 on printed circuit board 64 by radially displaced beams A and B causes the surface to generate florescent radiation within a hemispherical region as indicated generally by reference number 70. The cylindrical glass rods 72 collect the florescent radiation 70 and focus the collected radiation on fiberoptic bundle assemblies 74. The optical input window of assemblies 74 is divided into a first section 76, a second section 78 and a sandwiched section 80. Separate fiberoptic bundles couple the light received from sections 76, 78 and 80 of assembly 74 to separate photomultiplier tubes which are generally illustrated in FIG. 2 and designated as "PMT" and which are symbolically depicted in FIGS. 7A–7H where these separate photomultiplier tubes are symbolically represented by circles individually designated by reference numbers "1," "S," and "2." PMT-1 receives its optical input signal from section 76; PMT-2 receives its optical input signal from section 78; and PMT-S receives its optical input signal from section 80. For convenience of illustration in FIG. 2, separate groups of photomultiplier tubes have been depicted as being coupled to fiberoptic bundle assemblies 74, while in the preferred embodiment of the invention the separate outputs from both assemblies 74 are coupled to feed a single set of three photomultiplier tubes. For simplicity, glass rods 72 have been omitted from FIG. 2.

In the preferred embodiment of the invention, the width of the PMT-1 and PMT-2 windows equals two inches while the width of the window of PMT-S equals one inch. The manner of selecting various other window dimensions would be obvious to one of ordinary skill in the art.

In the following discussion, the term "first radiation detection means" refers to the first section 76 of fiberoptic bundle assembly 74, photomultiplier tube 1, and the interconnecting fiberoptic bundle. The term "second radiation detection means" refers to second section 78 of fiberoptic assembly 74, photomultiplier tube 2 and the interconnecting fiberoptic bundle. The term "sandwiched radiation detection means" refers to the sandwiched section 80 of fiberoptic bundle assembly 74, photomultiplier tube S and the interconnecting fiberoptic bundle.

Referring now to FIGS. 7A–7H, the operation of the information reading or information processing section of the laser inspection apparatus of the present invention will now be described in detail. In FIG. 7, circles designated as "1," "2," and "S," represent respectively the first and second photomultiplier tubes and the sandwiched photomultiplier tube.

The plurality of lines extending between the window 82 of fiberoptic bundle assembly 74 and the photomultiplier tubes represent the fiberoptic bundles which interconnect window 82 to the individual photomultiplier tubes. The pie-shaped group of rays designated by reference numbers 84 and 86 represent a two dimensional depiction of the conical section of florescent radiation generated from the fiberglass substrate of printed circuit board 64 which fall within the acceptance angle of the overlying fiberoptic bundle assemblies. The balance of the hemispherical section of florescent radiation designated in FIG. 12 by reference number 70 has not been illustrated in FIG. 7 since this other radiation lies outside of the acceptance angle of the fiberoptic bundles and has only a very limited effect on the operation of the present invention.

The graph lying immediately below scanned line 42 in each section of FIG. 7 illustrates the relative amplitude of the electrical output signal from the first, second and sandwiched photomultiplier tubes. The first or left hand section of each graph represents the relative magnitude of the electrical output signal from the first photomultiplier tube; the right hand graph represents the electrical output signal from the second photomultiplier tube; and the intermediate or sandwiched graph represents the relative amplitude of the electrical output signal from the sandwiched photomultiplier tube. The vertical lines with arrows included in each section of each graph are labelled to indicate whether the source of each electrical output signal was electromagnetic radiation produced by scan A or by scan B. Each amplitude line so indicated corresponds directly to the florescent radiation symbolically depicted immediately above the graph and designated by reference numbers 84 and 86. For the purpose of simplicity, the term first and second modulated scans will now be used to refer respectively to the florescent radiation induced as a result of illumination of the surface of the printed circuit board by scanned beams A and B.

FIG. 7A illustrates scans A and B generating first and second modulated scans 84 and 86 as the input beams A and B to the polygon mirror scanner 30 are crossing from one facet to an adjacent facet. During this dead time, no stabilized signal is available on scanned line 42 and the photomultiplier tubes are disabled. As illustrated in FIG. 7A, the cone of radiation generated in response to beam A falls outside of the acceptance angle of PMT-1 and produces a zero level output signal as confirmed by the underlying graph. At the same time, the cone of radiation 86 produced by beam B falls entirely within the boundaries of PMT-1 and generates a maximum or unity level output signal.

FIG. 7B illustrates a rightward displacement of beams A and B such that approximately fifty percent of the radiation from the first modulated scan 84 is detected by PMT-1 as confirmed by the one half of unity electrical output signal on the underlying graph. Beam B generates the second modulated scan 86 which equally illuminates PMT-1 and PMT-S. In the underlying graph, the decreasing intensity section of the graph designated by reference number 88 illustrates the electrical output signal contribution caused by beam B in PMT-1 while the upwardly sloping section 90 of the graph designates the electrical output signal from PMT-S caused by beam B. The sum of these two independent output signal contributions is equal to unity.

FIG. 7C illustrates the start of scan configuration of the laser inspection apparatus of the present invention. As indicated above, the sixty-fourth clock pulse actuates the information reading section of the present invention at this point and begins processing the electrical output signals from PMT-1, PMT-2 and PMT-S. As illustrated in FIG. 7C, the beam 84 is fully within boundaries of PMT-1 and produces a unity level output as indicated by the underlying graph. At the same time, beam 86 is fully within the boundaries of PMT-S and produces a unity level output.

In FIG. 7D, beam 84 has moved to the right hand boundary of PMT-1 while beam 86 has moved to a position where its trailing edge is aligned with the left hand boundary of PMT-2. In this configuration as indicated by the underlying graph, the output of both PMT-1 and PMT-2 is equal to unity.

As beams 84 and 86 move from the position illustrated in FIG. 7D to the positions illustrated in FIG. 7E, beam 84 partially illuminates both PMT-1 and PMT-S while beam 86 illuminates only PMT-2.

In FIG. 7F, the leading edge of beam 84 has reached the right hand boundary of PMT-S. Any further rightward displacement of beam 84 would illuminate both PMT-S and PMT-2. At the scan position illustrated in FIG. 7F, beam 86 illuminates only PMT-2.

In FIG. 7G, beam 84 illuminates both PMT-S and PMT-2 while beam 86 begins to pass beyond the right hand boundary of PMT-2.

As illustrated in FIG. 7H, beam 84 now fully illuminates only PMT-2 while beam 86 has passed beyond the boundary of PMT-2.

The beam position configuration illustrated in FIG. 7C defines the start of scan while the beam configuration depicted in FIG. 7F defines the end of scan. The output signals from the three photomultiplier tubes are not used during the beam configurations depicted in FIGS. 7A, 7B, 7G and 7H. When the beam position illustrated in FIG. 7D is reached, the signal processing means of the present invention switches from State 1 to State 2 in order to avoid cross talk which would otherwise occur as beam 84 moves into the reception zone of PMT-S. For the same reason, the end of scan is defined as the FIG. 7F configuration to avoid cross talk which would occur as beam 84 moves into the reception zone of PMT-2.

Figure 15A:
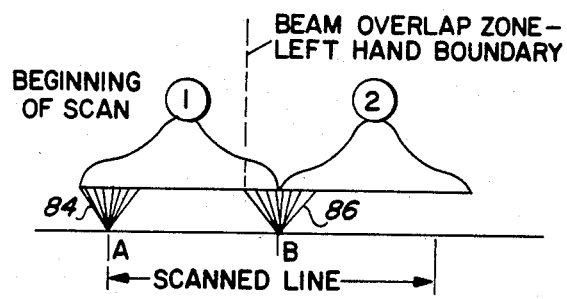
FIGS. 15A and 15B illustrate the cross talk problem encountered by segmented radiation collection means incorporating only two photomultiplier tube assemblies.

The source of the cross talk problem recited above will now be briefly described in connection with FIGS. 15A and 15B. FIG. 15A illustrates a dual photomultiplier tube detector. At the begining of scan configuration illustrated in FIG. 15A, beam 84 lies fully within the reception area of PMT-1 while beam 86 is simultaneously received by both PMT-1 and PMT-2. This beginning of scan configuration defines the lefthand boundary of a "beam overlap zone" where beam 86 overlaps into the reception zone of PMT-1.

Figure 15B:
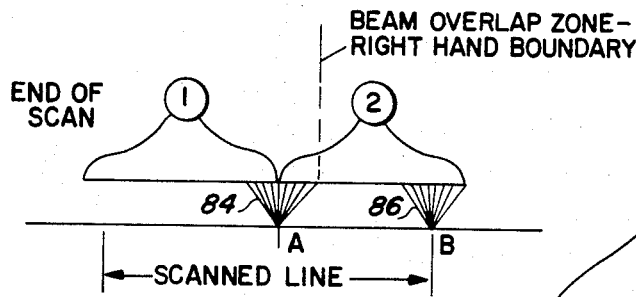
Figure 17A:
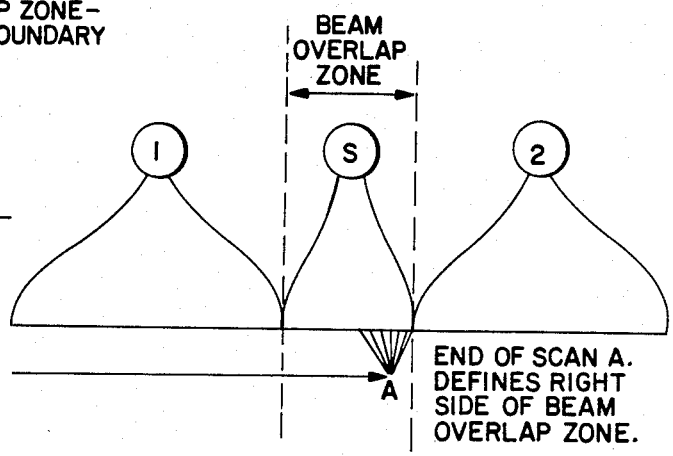
FIGS. 17A and 17B particularly illustrate the manner in which the first and second boundaries of the sandwiched radiation detection means of the present invention are determined and the relationship of those boundaries to the beam overlap zone.

At the end of scan configuration illustrated in FIG. 15B, beam 84 is detected by both PMT-1 and PMT-2 and thereby generates cross talk. The right hand boundary of beam 84 defines the right hand boundary of the beam overlap zone.

In a corresponding manner, the vertical dotted line designated by reference number 92 in FIG. 7C indicates the left hand boundary of the beam overlap zone defined by the left most displacement of the left side of beam 86. Similarly, the right hand boundary of the beam overlap zone is defined by the right-most displacement of the right side of beam 84 as illustrated by the vertically oriented dotted line identified by reference number 94 in FIG. 7F.

One part of the solution to the cross talk problem solved by the present invention resides in the utilization of a sandwiched photomultiplier tube assembly which has a left hand radiation reception boundary precisely aligned with the left hand boundary 92 of the beam overlap zone and a right hand radiation reception boundary precisely aligned with the right hand boundary 94 of the beam overlap zone. A second major element of the present invention which assists in totally eliminating cross talk resides in the utilization of the beam position signal to sum the electrical output signals from PMT-2 and PMT-S during State 1 illustrated in FIG. 7C and then by switching into State 2 in which the outputs from PMT-1 and PMT-S are summed. As will be explained below, the utilization of the sandwiched radiation detection means in combination with beam position signal directed switching totally eliminates the cross talk problems inherent in the segmented radiation collection means illustrated in FIG. 15.

Figure 10:
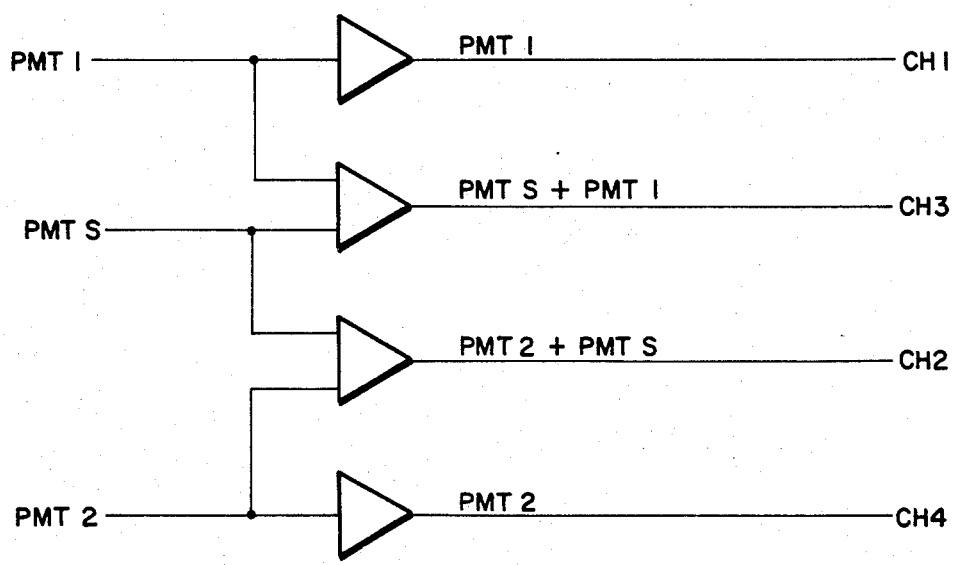
FIG. 10 is a conceptualized electrical schematic diagram particularly illustrating the manner in which the electrical output signals from the first and second radiation detection means are combined to produce four discrete electrical output signals.

Referring now to FIGS. 7 and 10 and to the State Table included below, the solution of the present invention to the cross talk problem discussed in connection with FIG. 15 will be discussed in detail.

STATE TABLE

| STATE | CHANNEL NO. | SELECTED PMT | BEAM READ |
| --- | --- | --- | --- |
| 1 | CH. 1 | PMT-1 | A |
| 1 | CH. 2 | PMT-S + PMT-2 | B |
| 2 | CH. 3 | PMT-1 + PMT-S | A |
| 2 | CH. 4 | PMT-2 | B |

During switching State 1 illustrated in FIGS. 7C and 7D, Channel 1 of the summing network illustrated in FIG. 10 provides an electrical output signal representative of the electrical output signal of only PMT-1. Since during the entirety of the scan angle corresponding to State 1 illustrated in FIGS. 7C and 7D, beam 84 is received exclusively by PMT-1, the Channel 1 output of the FIG. 10 summing network generates a signal directly analogous to beam 84 during State 1.

During this same State 1 time interval, beam 86 is received either by PMT-S alone or by both PMT-S and PMT-2. The outputs of PMT-S and PMT-2 are added by the FIG. 10 summing network to produce the Channel 2 output. The Channel 2 output is directly analogous to beam 86 during State 1.

During switching State 2 illustrated in FIGS. 7E and 7F, Channel 3 of the FIG. 10 summing network provides an electrical output signal representative of the electrical output signal of PMT-1 plus PMT-S. Since during the entirety of the scan angle corresponding to State 2 illustated in FIGS. 7E and 7F, beam 84 is received by both PMT-1 and PMT-S, the Channel 3 output of the FIG. 10 summing network generates a signal directly analogous to beam 84 during State 2.

During this same State 2 time interval, beam 86 is received exclusively by PMT-2. The Channel 4 output of the FIG. 10 summing network generates a signal directly analogous to beam 86 during State 2.

As indicated by the State Table depicted above, the signal processing means of the present invention switches from State 1 to State 2 at the next clock interval following the beam position illustrated in FIG. 7D.

During State 1, the Channel 1 output is representative of the signal produced by beam 84 or beam A, while the Channel 2 output is representative of the signal produced by beam 86 or beam B. During State 2, the Channel 3 output is representative of the signal produced by beam 84 or beam A while the Channel 4 output is representative of the signal produced by beam 86 or beam B. The signal processing means sequentially selects the appropriate output of the Channel 1/Channel 3 pair and the appropriate output of the Channel 2/Channel 4 pair to produce two outputs, one representing the beam A output and the other representing the beam B output.

At the next clock pulse immediately following the beam position illustrated in FIG. 7F, the signal processing means of the present invention disregards the outputs from PMT-1, PMT-2 and PMT-S. The unwanted cross talk produced during these subsequent timing intervals as illustrated in FIGS. 7G and 7H is therefore avoided.

Figure 16B:
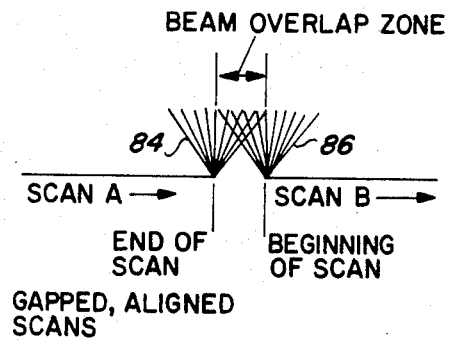
Figure 17B:
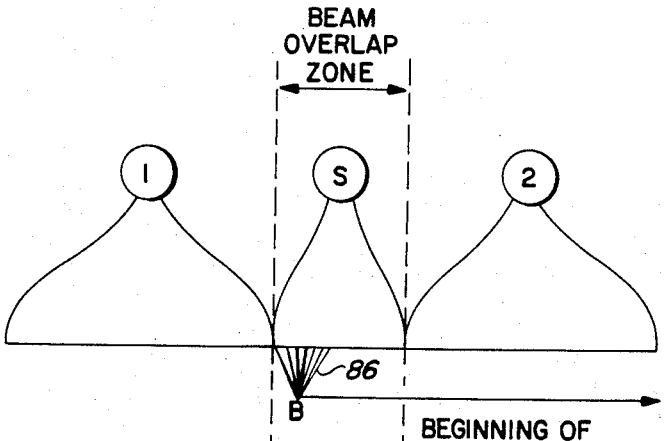
Figure 16C:
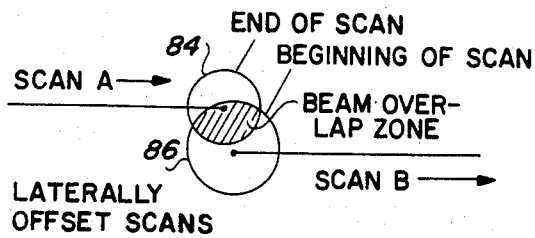

Referring now to FIG. 16, 16A illustrates that the segmented radiation collection means of the present invention can be used in connection with an optical scanner utilizing aligned but overlapping scans (FIG. 16A), aligned, spaced apart scans (FIG. 16B), or laterally offset scans which are sufficiently close together to create a beam overlap (FIG. 16C). The actual dimension of the beam overlap zone will be a function of many variables such as the acceptance angle of the fiberoptic bundles utilized, the spacing between the exposed ends of the fiberoptic bundle and the scanned plane and related variables. As is known to those of ordinary skill in the art, the switching of the PMT-S output to alternately be summed with the output of an adjacent PMT-1 or PMT-2 is typically implemented between clock pulses to avoid unwanted noise. In addition, it would be obvious to use four or more photomultiplier tubes to implement the cross talk elimination system of the present invention.

In other embodiments of the invention, it may be desirable to receive and process laser radiation directly reflected from the copper surface of a printed circuit board or equivalent surface rather than utilizing fluorescent radiation of a different wavelength emitted in response to laser radiation.

A variety of different types of signal processing circuits may be implemented in a manner well known to those of ordinary skill in the art. Processing circuitry for comparing information read from the surface of a printed circuit board or related surface with information corresponding to a standard or idealized surface is well known to those skilled in the art.

It will be apparent to those skilled in the art that the disclosed laser inspection apparatus may be modified in numerous other ways and may assume many embodiments other than the preferred forms specifically set out and described above. Accordingly, it is intended by the appended claims to cover all such modifications of the invention which fall within the true spirit and scope of the invention.

We claim:

1. An optical scanner for repetitively scanning a first line with first and second angularly displaced synchronized scans comprising:
   a. a light source for generating an input beam;
   b. means for receiving the input beam and generating first and second angularly displaced beams lying in first and second non-parallel planes;
   c. a polygon mirror scanner for receiving the first and second beams on a single facet and for generating first and second angularly displaced, non-parallel synchronized scans;
   d. facet to axis error correction means including
      a first cylindrical lens positioned in the optical path prior to said scanner;
      ii. a second cylindrical lens positioned in the optical path between said scanner and the scanned line for reconverging the first and second synchronized scans onto the first scanned line;
   redirecting means positioned in the optical path between said scanner and said second cylindrical lens for redirecting a portion of the first and second synchronized scans onto a timing plane to generate third and fourth non-coincident synchronized scans; and
   f. means for generating a beam position signal consisting of equally spaced, sequential pulses in response to the travel of the third or fourth synchronized scan along a second scanned line within the timing plane;

whereby the beam position signal is representative of the position of both the first and second synchronized scans along the first scanned line.

2. The optical scanner of claim 1 wherein the power axis of said second cylindrical lens is oriented parallel to the power axis of said first cylindrical lens.

3. The optical scanner of claim 1 wherein said beam position signal generating means includes a ruled transmission grating.

4. The optical scanner of claim 3 wherein said ruled transmission grating further includes a linear ruling.

5. The optical scanner of claim 4 wherein said linear ruling includes a plurality of equally spaced apart, alternating opaque and transparent sections.

6. The optical scanner of claim 5 wherein said beam position signal generating means produces a uniform series of optical timing pulses as the third synchronized scan is displaced along the second scanned line.

7. The optical scanner of claim 6 wherein said beam position signal generating means further includes means for converting the optical timing pulses into an electrical timing signal.

8. The optical scanner of claim 7 wherein said beam position signal generating means further includes a photomultiplier tube for converting the optical timing pulses into the electrical timing signal.

9. The optical scanner of claim 1 wherein said light source includes a laser.

10. The optical scanner of claim 3 wherein said ruled transmission grating is positioned to intercept third synchronized scan without intercepting the fourth synchronized scan.

11. The optical scanner of claim 10 wherein said ruled transmission grating includes a linear segment for modulating the intensity of the third synchronized scan without interference from the fourth synchronized scan.

12. The optical scanner of claim 11 wherein said beam position signal generating means includes means for intercepting the modulated output signal from said transmission grating and for converting the modulated optical output signal into an electrical beam position signal.

13. The optical scanner of claim 1 wherein said means for generating the first and second beams includes a beam splitter.

14. The optical scanner of claim 13 wherein said means for generating the first and second beams further includes first and second relay mirrors oriented to intercept one of the output beams from said beam splitter and for directing the intercepted beam into the second, non-parallel plane.

15. The optical scanner of claim 1 wherein said redirecting means includes a beam splitter.

16. The optical scanner of claim 15 wherein the first and second synchronized scans intercept said beam splitter with a relative positional displacement orthogonal to the first scanned line.

17. The optical scanner of claim 1 wherein said second cylindrical lens is positioned in proximity to the first scanned line.

18. The optical scanner of claim 1 further including a scan lens positioned in the optical path between said polygon mirror scanner and said redirecting means for providing straight line, constant velocity scans as said first and second synchronized scans are deflected through said scan lens.

19. The optical scan of claim 18 wherein said scan lens includes an f θ lens.

20. The optical scanner of claim 19 wherein said f θ lens includes a flat focal plane.

21. The optical scanner of claim 1 wherein the reflection of the first and second synchronized scans from the first scanned line produces first and second modulated scans.

22. The optical scanner of claim 21 further including:
  a. segmented radiation collection means for receiving the first and second modulated scans, including
    i. sandwiched radiation detection means having first and second boundaries and being positioned to collect radiation alternately emitted by the first and second modulated scans within a beam overlap zone defined by the beginning of the second modulated scan and by the end of the first modulated scan and for generating an electrical output signal representative of the first and second modulated scans within the beam overlap zone;
    ii. first radiation detection means having a third boundary positioned to collect radiation emitted by the first modulated scan from the beginning of the scan and a fourth boundary positioned adjacent to the first boundary of the sandwiched radiation detection means, wherein the first radiation detection means generates an electrical output signal representative of the first modulated scan as it moves between the third and fourth boundaries;
    iii. second radiation detection means having a fifth boundary positioned adjacent to the second boundary of said sandwiched radiation detection means and a sixth boundary positioned to collect radiation emitted by the second modulated scan at the end of the scan, wherein said second radiation detection means generates an electrical output signal representative of the second modulated scan as it moves between the fifth and sixth boundaries.

23. The optical scanner of claim 22 further including signal processing means for receiving the electrical output signals from said first and second radiation detection means and from said sandwiched radiation detection means and for selectively combining said signals in response to the beam position signal to generate first and second modulated output signals, wherein the first modulated output signal is representative of the information residing within the area scanned by the first scan and wherein the second modulated signal is representative of the information residing within the area scanned by the second scan.

24. The optical scanner of claim 23 wherein said optical scanner repetitively scans the surface of a printed circuit board.

25. Apparatus for reading information from a surface having an area illuminated by an optical scanner repetitively generating first and second angularly displaced, synchronized scans and a beam position signal representative of the position of the first and second scans where the first and second scans cause the area to emit radiation in the form of first and second modulated scans, said apparatus comprising:
  a. segmented radiation collection means for receiving the first and second modulated scans, including
    i. sandwiched radiation detection means having first and second boundaries and being positioned to collect radiation alternately emitted by the first and second modulated scans within a beam overlap zone defined by the beginning of the second modulated scan and by the end of the first modulated scan and for generating an electrical output signal representative of the first and second modulated scans within the beam overlap zone;
    ii. first radiation detection means having a third boundary positioned to collect radiation emitted by the first modulated scan from the beginning of the scan and a fourth boundary positioned adjacent to the first boundary of the sandwiched radiation detection means, wherein the first radiation detection means generates an electrical output signal representative of the first modulated scan as it moves between the third and fourth boundaries;
    iii. second radiation detection means having a fifth boundary positioned adjacent to the second boundary of said sandwiched radiation detection means and a sixth boundary positioned to collect radiation emitted by the second modulated scan at the end of the scan, wherein said second radiation detection means generates an electrical output signal representative of the second modulated scan as it moves between the fifth and sixth boundaries; and
  b. signal processing means for receiving the electrical output signals from said first and second radiation detection means and from said sandwiched radiation detection means and for selectively combining said signals in response to the beam position signal to generate first and second modulated output signals, wherein the first modulated output signal is representative of the information residing within the area scanned by the first scan and wherein the second modulated signal is representative of the information residing within the area scanned by the second scan.

26. The apparatus of claim 25 wherein said sandwiched radiation detection means includes a fiberoptic bundle having a window positioned in proximity to said surface for conveying the first and second modulated scans to energy conversion means and for converting the modulated scans into an electrical output signal.

27. The apparatus of claim 26 wherein said first radiation detection means includes a fiberoptic bundle having a window positioned in proximity to said surface for conveying the first modulated scan to energy conversion means and for converting the first modulated scan into an electrical output signal.

28. The apparatus of claim 27 wherein said second radiation detection means includes a fiberoptic bundle having a window positioned in proximity to said surface for conveying the second modulated scan to energy conversion means for converting the second modulated scan into an electrical output signal.

29. The apparatus of claim 28 wherein the windows of said first, second and sandwiched radiation detection means lie in the same plane.

30. The apparatus of claim 25 further including focusing means positioned between said surface and said segmented radiation collection means for collecting the radiation emitted from said surface and for focusing the radiation onto said segmented radiation collection means.

31. The apparatus of claim 30 wherein said focusing means further includes a cylindrical lens.

32. The apparatus of claim 31 wherein said first and second radiation detection means and said sandwiched radiation detection means further include means for converting the optical signals processed by said radiation detection means into discrete electrical output signals.

33. The apparatus of claim 32 wherein said signal processing means further includes signal combining means for selectively combining the output of said first and second radiation detection means and said sandwiched radiation detection means into four discrete electrical output channels.

34. The apparatus of claim 33 wherein said signal processing means further includes timed switching means for combining selected pairs of the four discrete electrical output channels from said signal combining means at predetermined beam positions to generate the first and second modulated output signals.

35. The apparatus of claim 25 wherein said surface constitutes the surface of a printed circuit board.

* * * * *